United States Patent [19]

Buese

[11] Patent Number: 5,014,403
[45] Date of Patent: May 14, 1991

[54] METHOD OF MAKING A STRETCHABLE ORTHOPAEDIC FIBERGLASS CASTING TAPE

[75] Inventor: George J. Buese, East Brunswick, N.J.

[73] Assignee: Johnson & Johnson Orthopaedics, Inc., New Brunswick, N.J.

[21] Appl. No.: 476,191

[22] Filed: Feb. 7, 1990

[51] Int. Cl.⁵ .................. D06H 7/22; A61F 5/04; A61F 13/04

[52] U.S. Cl. .................................. 28/170; 128/90; 128/156; 428/253

[58] Field of Search .................. 28/168, 170

[56] References Cited

U.S. PATENT DOCUMENTS

| | | | |
|---|---|---|---|
| 3,332,416 | 7/1967 | Brickman et al. | 128/156 X |
| 3,686,725 | 8/1972 | Nisbet et al. | 428/273 X |
| 3,787,272 | 1/1974 | Nisbet et al. | 428/253 X |
| 3,881,473 | 5/1975 | Corvi et al. | 128/156 X |
| 3,882,857 | 5/1975 | Woodall, Jr. | 128/156 X |
| 4,323,061 | 4/1982 | Usukura | 128/156 X |
| 4,376,438 | 3/1983 | Straube et al. | 523/111 X |
| 4,411,262 | 10/1983 | von Bonin et al. | 128/90 |
| 4,433,680 | 2/1984 | Yoon | 128/90 |
| 4,502,479 | 3/1985 | Garwood et al. | 128/90 |
| 4,609,578 | 9/1986 | Reed | 428/251 X |
| 4,668,563 | 5/1987 | Buese et al. | 428/230 |

Primary Examiner—Werner H. Schroeder
Assistant Examiner—John J. Calvert
Attorney, Agent, or Firm—Michael Q. Tatlow

[57] ABSTRACT

A method of making a non raveling stretchable fiberglass fabric by knitting an elastic yarn under tension into the fabric in the length direction, releasing the tension from the elastic yarn to compact the fabric and removing the elastic yarn from the fabric.

6 Claims, 2 Drawing Sheets

BAR 1  BAR 2  BAR 3

BAR 1  BAR 2  BAR 3

BAR 1  BAR 2  BAR 3  BAR 4

METHOD OF MAKING A STRETCHABLE ORTHOPAEDIC FIBERGLASS CASTING TAPE

FIELD OF THE INVENTION

The present invention relates to an improved fiberglass casting tape. The casting tapes of the present invention have little tendency to fray or ravel and have substantial extensibility in their length direction which results in improved conformability, and thus allows better application of the casting tapes to the patient. The improved conformability results in a cast which better fits or conforms to the patient's limb.

BACKGROUND OF THE INVENTION

Plaster of Paris casts have been in use to immobilize body members or limbs for some time. In recent years, the plaster of Paris bandages have been supplemented and, to some extent, superseded by synthetic casting tapes or bandages which employ polymeric materials on a substrate. The polymeric materials are of the type that have been cured by exposure to ultra violet light or which would cure when reacted with water. Examples of the ultra violet light cured cast can be found in U.S. Pat. No. 3,881,473. More recently, water-cured or water-reactive polyurethane compositions have been used in forming orthopedic casts and the polyurethane compositions have largely supplanted other polymeric synthetic casting materials. The polyurethane casting materials are of the type which are disclosed in U.S. Pat. Nos. 4,376,438 and 4,411,262.

The fibrous substrate used in the synthetic casting tapes may be made from any natural or synthetic fiber including a fiberglass material. The fiberglass materials offer advantages in terms of strength of the finished cast when compared to other fibers and various constructions of fiberglass fabrics have been used for the substrates for synthetic casting tapes. The patents mentioned above disclose the use of different fiberglass materials as the substrate for casting tapes. In addition, U.S. Pat. Nos. 3,686,725, 3,787,272 and 3,882,857 disclose specific fiberglass materials, or the treatment of fiberglass materials, to produce fiberglass substrates which are particularly suitable for use in orthopedic casts.

U.S. Pat. No. 4,323,061 discloses a cast substrate made from a combination of glass fibers and a second fiber such as cotton, flax, rayon, wool, acrylic resin, nylon, polytetrafluoroethylene or polyester. The purpose of the second fiber in the substrate is to hold the curable resin on the substrate.

U.S. Pat. No. 3,332,416 discloses a plaster of Paris cast bandage with a woven substrate made with a combination of elastic and inelastic fibers.

U.S. Pat. No. 4,609,578 discloses a fiberglass substrate for casting tapes which has an extensibility of at least 20% and up to 25% to 35%. The fiberglass substrate is heat-set to prevent fraying. Care must be taken when handling of the fabric after knitting and before and after heat treatment to avoid applying undue tension to the fabric which would distort the knots and loops, i.e. stretch the fabric, and permanently lose some of the stretch of the fabric.

U.S. Pat. No. 4,668,563 discloses a cast substrate made from a combination of glass fibers and an elastomeric highly extensible fiber. The substrate has a stretch of from 40 to 200%. The elastomeric fiber is selected or is treated to insure that it is compatible with the water curable polyurethane prepolymer employed in the casting tape. Although the conformability of the tape disclosed is excellent, the presence of the elastomeric fiber in the substrate can cause storage stability or shelf life problems or add cost to the product because of the treatment of the elastomeric fiber that is required to insure longer shelf life. The presence of the elastomeric fiber in the finished product also necessitates a secondary process step, i.e. coating the fabric with a binder, to reduce fraying or ravel.

SUMMARY OF THE PRESENT INVENTION

The present invention provides an orthopedic casting tape which has a substrate which is all fiberglass does not fray or ravel but which has a very high degree of extensibility. The casting tape of the present invention is knitted with an elastic fiber in the length direction of the fabric which acts to compact or gather the fabric in the length direction when the fabric is removed from the knitting machine. The elastic fiber is subsequently removed from the fabric by a heat treatment process which removes the elastic yarn and heat sets the fabric in a contracted configuration with little or no fraying or raveling. The removal of the elastic fiber avoids the problems of storage stability which may be caused by the presence of the elastomeric fiber in the finished casting tape.

The presence of the elastic fiber in the knitted fabric allows the fabric to be handled normally, i.e. without undue regard to tension, until the elastic fiber is removed from the fabric. After the elastic fiber is removed from the fabric, some care should be taken to avoid applying tension to the fabric. However since the fabric is heat set by the process which eliminates the elastic yarn and therefore has some memory, normal handling during processing will not cause a major loss of stretch. Also, since the elastic fiber is removed from the fabric, the concerns of the reactivity of the water curable resin with the elastic fiber and the resultant storage stability or shelf life problems are not present in casting tapes made from the fabric of the present invention.

The purpose of the use of the elastic fiber is to compact or gather the fabric when the fabric is removed from the knitting machine. When the fabric is knitted the elastic yarn is stretched by being fed under predetermined tension to the knitting machine. The degree of tension or stretch of the elastic fiber or yarn will depend on the percent stretch desired in the final fabric. Increasing the tension in the elastic fiber results in more stretch in the fabric. When the knitted fabric is removed from the knitting needles on the machine, the stretched elastic fibers exert a force on the fabric which pulls the fabric in the length direction. The elastic fibers pull the courses of the fabric into closer proximity to each other thereby causing the fabric to contract. For example, a fabric of the present invention may be knitted with about 12 courses per inch and when the fabric is removed from the knitting machine and gathered by the elastic yarn the fabric may have 20 courses per inch. The fabric retains its compacted or gathered states to a substantial degree even after the elastic fibers are removed from the fabric by the heat treatment process because the fiberglass yarns are heat set in the contracted state which imparts a "spring like" memory to them.

The compacted or gathered fabric has a greater extensibility than a similar fabric made not using an elastic fiber.

DETAILED DESCRIPTION OF THE INVENTION

Figure 1:
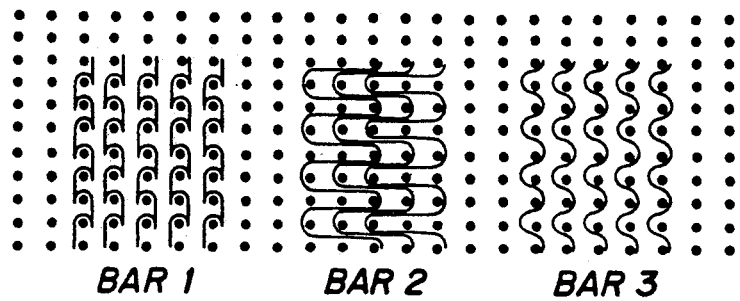
FIGS. 1 and 2 are three bar Raschel knits in which bar 1 performs a simple chain stitch and bars 2 and 3 perform lapping motions to lay in yarn.

The substrate of the casting tape of the present invention is knitted with a combination of continuous filament fiberglass and elastic filaments or yarns. Fiberglass substrates are generally characterized as made from filaments which are formed into yarn, sized and knitted into a desired construction. In the present invention the substrates are knitted on a Raschel Knitting Machine having 6 to 28 needles per inch. The cast substrate fabrics of the present invention are knitted fabrics which combine high modulus fiberglass with an elastomeric highly extensible fiber when the fabric is knitted. The elastomeric extensible fiber may be a natural rubber or a synthetic elastomer such as polyisoprene, polybutadiene, copolymers of a diene and styrene, copolymers of acrylonitrile and a diene or polychloroprene, copolymers of chloroprene and other monomers, ethylene propylene elastomers including ethylene propylene copolymers and ethylene propylene diene terpolymers, and thermoplastic elastomers which are block copolymers of styrene and butadiene or isoprene. The elastomeric extensible fiber may also be a spandex (polyurethane) fiber. The most common commercially available elastic yarns are natural rubber and spandex. Natural rubber has been used as the elastic yarn in the process of forming the substrate of the present invention.

The extensible fiber is present in the knit fabric in the warp or wale fibers, i.e., machine direction, but not in the fill fibers. The elastic or extensible fiber cannot be the fiber used to form the loop or chain stitch as the elastic fiber will eventually be removed from the fabric. Preferably about 0.25 to 25% of the fibers based on the total volume of fibers in the fabric are extensible. The knitted fabric, prior to the removal of the elastic fiber, should have a stretch in the length direction of at least 70% and up to 200%. The process of removing the extensible fiber by a heat treatment process could reduce the stretchability by some amount, 50% or more, of the stretch of the fabric prior to heating. Therefore, the preferred extensibility of the fabric, before heating to remove the elastic extensible fiber, is between 70% and 200%.

Since the elastic fiber used in the present invention will be removed from the substrate before the substrate is coated with the polyurethane prepolymer, i.e. a water curable isocyanate terminated resin, there is no concern of the possible reaction between the elastic fiber and the polyurethane prepolymer.

The knit patterns that may be used in the manufacture of the substrates of the present invention are numerous. Generally, the fabrics are knitted using a three bar knitting machine, one bar for the elastic thread and two bars for the fiberglass. In the knitted substrates of the present invention the elastic yarn must give the fabric stretch in the length direction of the fabric. The elastic yarn may be in bar 3, of a 3-bar or possibly bar 4 of a 4 bar Raschel knit construction fabric. As previously indicated the elastic yarn in the present invention should not be in the chain stitch. The elastic yarn may be intermittently spaced in the fabric. There need not be an elastic fiber for every needle employed in knitting the fabric. The elastic fiber need only be present in the fabric in a sufficient amount to give the desired compaction to the fabric when the fabric is removed from the knitting machine.

The third bar, and the fourth bar if used, could be used to lay in fiberglass in a zig-zag or a sinusoidal pattern which would increase the crush strength of the final cast by comparison to transversely laid in yarns in these positions. The elastic yarn may be in bar 3 in 3-bar knit or in bars 3 and/or 4 in a 4-bar knit fabric. The tension in the elastic yarn during the knitting process is important. The tension in the elastic yarn should be controlled to cause the fabric to gather or bunch uniformly to the desired degree when it is released from the knitting machine. When the finished heat treated fabric is stretched, the extensibility is achieved as the gathers are pulled out and any further stretch or extensibility of the fabric is limited by the loops in the chain stitch. The preferred fabric is a 3 bar knit with the elastic yarn in bar 3.

Typical bar patterns for the knit fabric substrates of the present invention are shown in the drawings.

FIG. 1 is a three bar pattern with the elastic thread on bar 3 and fiberglass on bars 1 and 2.

Figure 2:
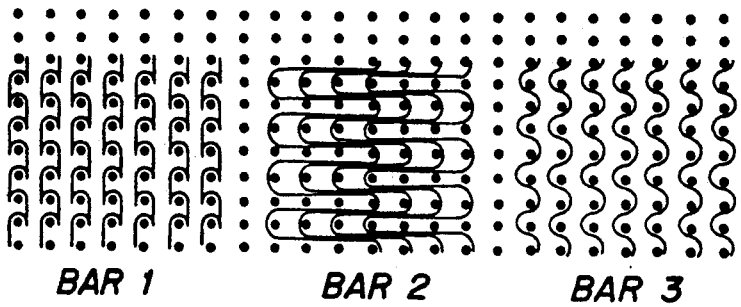

FIG. 2 is a three bar pattern in which the elastic thread is on bar 3 and fiberglass is on bars 1 and 2. This fabric would be heavier than the fabric of FIG. 1 as more fiberglass would be added to the fabric by bar 2.

Figure 3:
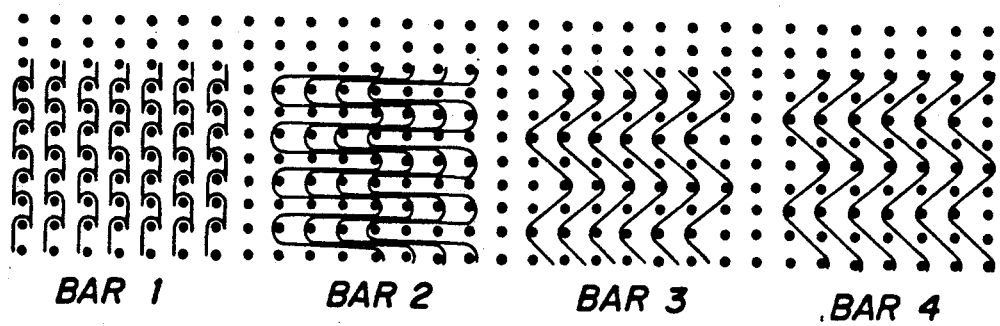
FIG. 3 is a four bar Raschel knit in which bar 1 performs a simple chain stitch and bars 2, 3 and 4 perform lapping motions to lay in yarn.
Figure 4:
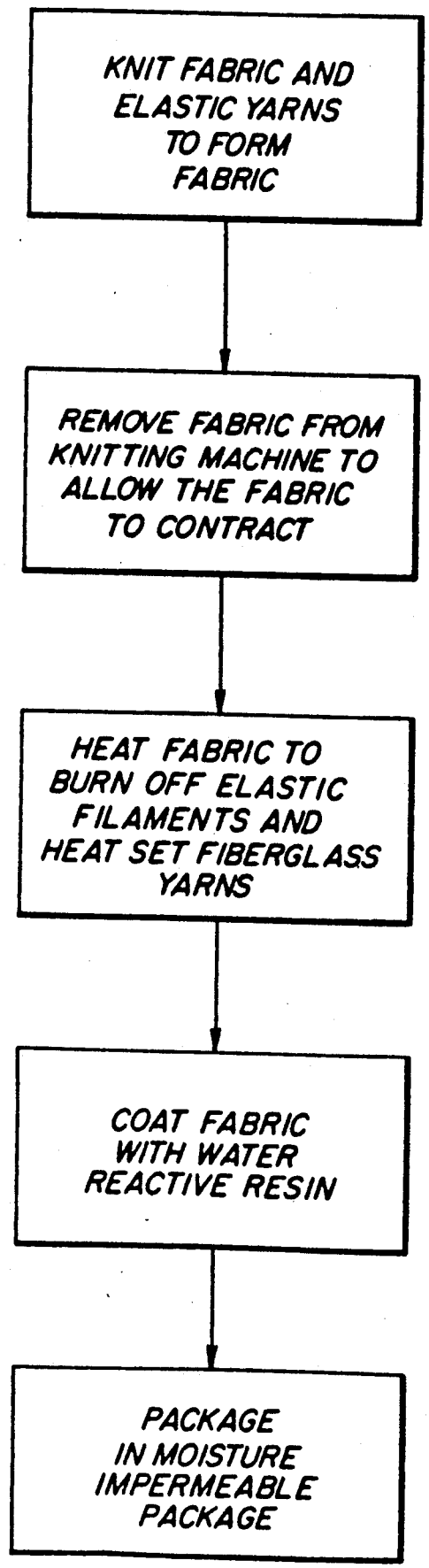
FIG. 4 is a block diagram of the steps of the process of the present invention.

FIG. 3 is a four bar pattern in which the elastic thread is on bar 3 or 4.

It should be understood that the above bar patterns may be modified. For example, the pattern of FIG. 3 may be employed with an elastic thread in bars 3 and 4 and fiberglass yarn in bars 1 and 2.

Also, the patterns of FIGS. 1 and 2 could be modified by employing a zig-zag pattern on bar 3 similar to that shown in bar 3 or bar 4 of FIG. 3. The particular knit pattern is not important as long as the fabric is compacted by the tension of the elastic yarn when the fabric is removed from the knitting machine.

The elastic fiber is removed from the fabric by heating the fabric in an oven at a temperature sufficiently high to burn off the elastic yarn and set the fabric in the contracted state. This can be accomplished by heating the fabric in an oven at a temperature between 400° F. and about 850° F. Heating the fabric to temperatures above about 1000° F. should be avoided as subjecting the fiberglass to temperatures of about 1000° F. can weaken the fiberglass yarns in the fabric which may result in reduced strength of casts made from such fabrics. Rapid burning of the elastic yarn should be avoided as this can increase the temperature of the fiberglass high enough to cause breakage of the fiberglass yarns.

The burning conditions can be varied depending on the particular elastomeric fiber used but the heat treatment must be sufficient to set the fiberglass yarns in the contracted configuration.

After the fabric is treated to remove the elastic yarn, the fabric should be carefully handled so that it is not stretched sufficiently to pull the gathers completely out of the fabric during the winding, coating and other casting tape manufacturing procedures.

EXAMPLE I

A fabric was knitted on a 24-gauge Raschel knitting machine using a 3-bar configuration as shown in FIG. 1. The first bar contained DE75 1/0 fiberglass yarn, the second bar contained the same fiberglass, and the third bar contained a natural rubber thread designated L83 from J. P. Stevens. The rubber thread was fed to the knitting machine under sufficient tension so that when the fabric was removed from the knitting machine and was allowed to contract by the action of the elastic yarn, the fabric had a machine direction stretch of 75%. The contracted fabric was then formed into a loose skein and placed in an oven at a room temperature. The temperature of the oven was raised to 450° F. during a period of two hours and held at 450° F. for 90 minutes. The temperature of the oven was then raised to 600° F. over a period of one hour and held at that temperature for one hour. The oven was then heated to a temperature of 695° F. over a period of one hour and held at that temperature for six hours. The oven was then allowed to cool to room temperature and the fabric removed for subsequent use as a substrate for a water reactive polyurethane casting tape. When the elastic fiber had been removed from the fabric samples the fabric had an elongation of about 35% (between 32% and 37%). The fabric was coated at 42% add on, with a water reactive with a polyurethane prepolymer of the type disclosed in U.S. Pat. No. 4,433,680 the disclosure of which is incorporated herein by reference and used in commercially available polyurethane casting tapes. The resulting casting tape was evaluated and was found to have improved conformability when compared to casting tapes made with heat set fiberglass coated with the same resin.

What is claimed is:

1. A method of forming an orthopedic casting tape comprising;
    knitting a fabric employing fiberglass yarns in the chain stitch of the fabric, and elastic yarns in the length direction of the fabric, the elastic yarn being present in a sufficient quantity to give the fabric a stretch before heating of at least 70%;
    removing the fabric from the knitting machine and allowing the power of the elastic filament to contract the fabric;
    heating the contracted fabric to burn off the elastic fiber in the fabric and heat set the fiberglass yarns in the fabric;
    coating the contracted fabric with a water reactive isocyanate terminated resin; and
    packaging the coated fabric in a moisture impermeable package until ready for use.

2. The method of claim 1 in which the fabric has a stretch before heating of between 70% and 200%.

3. The method of claim 1 in which the elastic filament is a natural rubber yarn.

4. The method of claim 1 in which the elastic filament is a polyurethane yarn.

5. The method of claim 1 in which the temperature at which the fabric is heated to burn off the elastic yarn is between 200° C. and 480° C.

6. The method of claim 1 in which the fabric has a stretch after heating of between 30% and 100%.

* * * * *